(12) United States Patent
Zhao

(10) Patent No.: US 9,402,681 B2
(45) Date of Patent: Aug. 2, 2016

(54) MAGNETIC MOXIBUSTION DEVICE

(71) Applicant: CHONGQING HAPPYALL MEDICAL INSTRUMENT LIMITED COMPANY, Chongqing (CN)

(72) Inventor: Baixiao Zhao, Beijing (CN)

(73) Assignee: CHONGQING HAPPY ALL MEDICAL INSTRUMENT LIMITED COMPANY, Chongqing (CN)

( * ) Notice: Subject to any disclaimer, the term of this patent is extended or adjusted under 35 U.S.C. 154(b) by 225 days.

(21) Appl. No.: 14/186,700

(22) Filed: Feb. 21, 2014

(65) Prior Publication Data

US 2014/0228618 A1    Aug. 14, 2014

Related U.S. Application Data

(63) Continuation of application No. PCT/CN2011/079148, filed on Aug. 31, 2011.

(51) Int. Cl.
*A61N 2/00* (2006.01)
*A61B 18/14* (2006.01)
(Continued)

(52) U.S. Cl.
CPC ............... *A61B 18/14* (2013.01); *A61H 39/06* (2013.01); *A61N 2/002* (2013.01); *A61N 2/06* (2013.01); *A61B 2018/064* (2013.01); *A61H 2201/10* (2013.01)

(58) Field of Classification Search
CPC .. A61B 18/14; A61B 2018/064; A61B 18/06; A61H 2201/10; A61H 39/06; A61N 2/002–2/12
USPC .............................................. 601/15; 606/27
See application file for complete search history.

(56) References Cited

U.S. PATENT DOCUMENTS

2002/0165527 A1* 11/2002 Won ....................... A61B 18/06
606/27
2004/0267171 A1    12/2004 Wells et al.

FOREIGN PATENT DOCUMENTS

CN        1236605        12/1999
CN        2696628        5/2005
(Continued)

OTHER PUBLICATIONS

Office Action from corresponding Japanese application, dated Jan. 22, 2015, and English machine translation thereof, 8 pages total.

*Primary Examiner* — Charles A Marmor, II
*Assistant Examiner* — Lauren Querido
(74) *Attorney, Agent, or Firm* — Hamre, Schumann, Mueller & Larson, P.C.

(57) ABSTRACT

A magnetic moxibustion device includes a moxibustion canister in which a moxa column (5) is hangs through a moxa column mounting base. The moxa column mounting base is mounted on the moxibustion canister in a detachable manner through a magnetic attraction structure. A magnet guiding needle (3) is further disposed in the moxa column mounting base, which passed through the moxa column (5). The magnetic field of the magnetic attraction structure is guided out of the moxibustion canister through the needle (3) and applied to the human body moxibustion application position, so as to perform the moxibustion therapy and the magnet therapy at the same time. A side wall of the moxibustion canister is provided with several air inlets (7) and air outlets (11), so the combustion speed of the moxa column (5) can be adjusted through the size of the air outlets, thereby adjusting the temperature and time of the moxibustion.

20 Claims, 15 Drawing Sheets

(51) Int. Cl.
*A61H 39/06* (2006.01)
*A61N 2/06* (2006.01)
*A61B 18/06* (2006.01)

(56) References Cited

FOREIGN PATENT DOCUMENTS

| | | | | |
|---|---|---|---|---|
| CN | 2863096 | | 1/2007 | |
| CN | 201211314 | | 3/2009 | |
| CN | 201342082 | Y * | 11/2009 | |
| CN | 101632620 | | 1/2010 | |
| CN | 201492655 | U * | 6/2010 | |
| CN | 201529262 | | 7/2010 | |
| CN | 201529263 | | 7/2010 | |
| JP | 57-154430 | | 9/1982 | |
| JP | 57154430 | U * | 9/1982 | |
| JP | 2002-136568 | | 5/2002 | |
| JP | 2002-315811 | | 10/2002 | |
| KR | 20100092146 | | 8/2010 | |
| TW | 542733 | | 7/2013 | |

\* cited by examiner

MAGNETIC MOXIBUSTION DEVICE

TECHNICAL FIELD

The present invention relates to a traditional Chinese medicine acupuncture therapy device, and particularly to a moxibustion device acting on a point of a human body.

BACKGROUND ART

Moxibustion is an important branch of acupuncture therapy and is one of important means in traditional Chinese medicine cure of disease. The acting ways of moxibustion include warm stimulation on the point during moxa combustion process, pharmacological action of volatile matters in moxa combustion and so on. Conventional moxibustion mostly comprises moxa column moxibustion and moxa stick moxibustion. However, whether moxa column moxibustion or moxa stick moxibustion, there is much smog released during moxibustion, which causes the patient and the doctor to difficultly withstand. At the same time, there is a risk that the patient may be scalded by the dispersed ash being burning during moxibustion. Furthermore, since the moxa column or moxa stick has not been packed by a container, moxa and thermal power is mostly wasted; temperature is not stable during moxibustion, the curative effect is affected, and the operation is not convenient, which have greatly limited the widespread applications of moxibustion.

Now, there are smokeless moxibustion product, moxibustion box and the like in the market. Most common smokeless moxibustion product is smokeless moxa stick, which is mixed mostly by carbonized moxa and wood carbon in certain proportions, the smoke is not strong during combustion, it is relatively convenient to use, however, since the material used is not moxa used by traditional moxibustion and naturally loses the moxibustion therapy effect offered by the traditional moxibustion, such smokeless moxibustion has not been the traditional moxibustion. Thousands of years ago, it was discussed and compared about the moxibustion in traditional Chinese medicine, it was concluded that moxa has the best moxibustion therapy effect compared to the other materials. Just as such, moxa was selected and fixed as moxibustion material in the development of thousands of years, there has been such "moxa" moxibustion. Accordingly, moxibustion can be considered as "moxa" moxibustion only in case that it selects moxa as the moxibustion material, and can not in other cases.

Whether the mixture mixed by carbonized moxa and wood carbon in certain proportions or pure carbonized moxa, has a varied property. Such moxa stick has a very high temperature of combustion, and it is easy to break and disperse during combustion, thereby causing the patient to scald, bubble, infect and so on. Although bubble moxibustion may be used in curing some special disease, such moxibustion therapy is disadvantageous to widely use, which is not easily to be accepted by people nowadays. Smokeless moxa stick differs from traditional moxa both in form and in nature, and basically, can not be called as "moxa" moxibustion; furthermore, the curative effect of traditional moxibustion is caused by a combination of various factors, including the pharmic property of moxa and all kinds of radiations produced during combustion, and is not a simple warm effect which now commercially available smokeless moxibustion basically only has so that it can not obtain true moxa moxibustion curative effect. Furthermore, the moxibustion temperature is still not stable, low or high, during moxibustion therapy using smokeless moxa stick, and is not easy to induce moxibustion transducing phenomena, thereby affecting curative effect.

The commercially available moxibustion box can control the combustion speed and temperature to some extent, but the controlling ranges is limited, also, the moxa column is not convenient to install, the moxibustion box is easy to overturn, and there is also the risk that the patient may be scalded by the dispersed ash and that fire occurs.

CONTENTS OF INVENTION

To address the aforesaid drawbacks of the prior art, an object of the present invention is to provide a magnetic moxibustion device which has both moxibustion therapy and magnetic therapy functions, has the adjustable moxibustion temperature, and is safety and convenient to use.

To achieve the above object, a magnetic moxibustion device is provided, which comprises a moxibustion canister with a sealed upper end, and a moxa column is hanged in the moxibustion canister through a moxa column mounting base. The upper end of the moxa column mounting base is mounted on a top wall of the moxibustion canister in a detachable manner through a magnetic attraction structure. A magnet guiding needle extending toward a lower end of the moxibustion canister is further disposed in the moxa column mounting base, the magnet guiding needle passes through the moxa column, wherein the magnetic field of the magnetic attraction structure is guided out of the lower end of the moxibustion canister through the magnet guiding needle, and is applied to the human body moxibustion application position, so as to perform the moxibustion therapy and the magnet therapy at the same time.

Further, the magnetic attraction structure is comprised of a movable portion and a fixed portion, at least one of which is made of magnet, wherein, the movable portion and the fixed portion are detachably connected with each other in a mutual attraction way, the fixed portion is fixed onto the top wall of the moxibustion canister, the movable portion is fixed with the upper end of the moxa column mounting base, and the magnet guiding needle is connected with the movable portion.

Further, both the movable portion of the magnetic attraction structure and the magnet needle are made of ferromagnetic material, and the movable portion is directly formed of a metal ring manufactured by bending the upper end of the magnet guiding needle.

Further, both the fixed portion and the movable portion of the magnetic attraction structure are of a sheet structure, thereby the corresponding forming fixed sheet and movable sheet respectively.

Further, the moxa column mounting base is directly formed by the magnet guiding needle, and the moxa column is hanged in the moxibustion canister by the magnet guiding needle being inserted into the moxa column.

Further, the moxa column mounting base includes a moxa column fixing sleeve, the movable sheet is fixed with the upper end of the moxa column fixing sleeve, the magnet guiding needle is located within the moxa column fixing sleeve, and the moxa column is inserted in the moxa column fixing sleeve through one end thereof.

Further, in the moxa column fixing sleeve is provided with a heat-insulated structure for obstructing heat during the combustion of the moxa column transferring to the movable sheet, wherein the heat-insulated structure is formed by a partition or cylindrical wood block provided within the moxa column fixing sleeve.

Further, on the side wall of the moxa column fixing sleeve is provided with a through hole for discharging high-temperature gas produced within the moxa column fixing sleeve during the combustion of the moxa column.

Further, within the moxibustion canister is provided with a clamp spring or a snap ring with a center bore, the clamp spring or a snap ring is adhesively fixed to the top wall or side wall of the moxibustion canister and clips the sleeve of the moxa column fixing sleeve, and the moxa column fixing sleeve is radially and detachably fixed by the clamp spring or a snap ring.

Further, the magnet guiding needle is inserted to at least one third of the full-length of the moxa column or is inserted through the moxa column from up to down.

Further, the moxibustion canister is a cylindrical barrel, a side wall of the moxibustion canister is provided with several air inlets in peripheral and uniform distribution way close to the lower end of the moxibustion canister, and is provided with several air outlets in peripheral and uniform distribution way close to the upper end thereof.

Further, the moxibustion canister consists of a moxibustion canister body and a moxibustion canister lid, the moxibustion canister lid hermetically covers the upper end of the moxibustion canister body in an inserting or sleeving way, and partly overlaps with the moxibustion canister along an axis of the moxibustion canister body, the air outlets are positioned at the location where the moxibustion canister body overlaps with the moxibustion canister lid, and radially extend through both the moxibustion canister body and the moxibustion canister lid, so that the moxibustion canister lid can be rotated relative to the moxibustion canister body, thereby adjusting the opening size of the air outlets.

Further, within the moxibustion canister body there is a screen partition which is positioned beneath the moxa column and has a gap with the lower end of the moxibustion canister body to ensure that it can not be in contact with the skin at the moxibustion site of the human body.

Further, on each of the inner surfaces of the moxibustion canister body, the moxibustion canister lid and the screen partition, is provided with a heat reflecting film having flame retardant characteristic.

Further, at the lower end of the moxibustion canister body is provided with a ring-shaped moxibustion seat radially projecting from the exterior surface of the moxibustion canister body, and a medical adhesive tape is sleeved on the moxibustion canister body, which can fix the whole magnetic moxibustion device to the moxibustion site of the human body by pressing against the upper surface of the ring-shaped moxibustion seat.

The present invention may also be another embodiment described below:

A magnetic moxibustion device, wherein, moxa column combustion chamber is composed of a moxibustion canister and a moxibustion canister lid hermetically covering the moxibustion canister, a moxa column is hanged in the moxibustion canister lid through a moxa column mounting base, the moxa column mounting base is comprised of a magnetic sheet and a moxa column fixing sleeve, the upper end of the moxa column mounting base is adhesively fixed to the top wall of the moxibustion canister lid via the magnetic sheet, a magnet guiding needle extending toward a lower end of the moxibustion canister is further disposed in the moxa column mounting base, the magnet guiding needle passes through the moxa column, wherein, the magnetic field of the magnetic sheet is guided out of the lower end of the moxibustion canister through the magnet guiding needle, and is applied to the human body moxibustion application position, so as to perform the moxibustion therapy and the magnet therapy at the same time.

Further, the upper end of the moxa column fixing sleeve is adhesively fixed to the magnetic sheet, in the moxa column fixing sleeve is further provided with a heat-insulated structure for obstructing heat during the combustion of the moxa column from transferring to the magnetic sheet, and the heat-insulated structure is formed by a cylindrical wood block provided within the moxa column fixing sleeve; the magnet guiding needle is provided within the moxa column fixing sleeve, the top end of the magnet guiding needle has a ferromagnetic sheet for attracting the magnet guiding needle onto the magnetic sheet, the ferromagnetic sheet and the magnet guiding needle are formed integrally; on the side wall of the moxa column fixing sleeve is provided with a through hole for discharging high-temperature gas produced within the moxa column fixing sleeve during the combustion of the moxa column.

Further, within the moxibustion canister lid is provided with a clamp spring or a snap ring with a center bore, the clamp spring or a snap ring is adhesively fixed to the top wall or side wall of the moxibustion canister lid and clips the sleeve of the moxa column fixing sleeve, and the moxa column fixing sleeve is radially and detachably fixed by the clamp spring or a snap ring.

Compared to the prior art, the present invention has one or more of advantages as follows:

(1) moxa column mounting base is provided, in which the moxa column can be detachably installed, so the moxa column can be replaced many times during moxibustion, the magnetic moxibustion device can be used many times.

(2) The magnetic moxibustion device is provided with a magnet matching with the moxa column and can carry out magnetic therapy while carrying out moxibustion therapy, thereby improving the curative effect.

(3) In using the magnetic moxibustion device, ash produced by the combustion of the moxa column within the moxibustion canister is not dispersed and is collected around the magnet guiding needle, which may not scald the patient and eliminate the potential safety hazard of firing other articles.

(4) The medical adhesive tape attached by the magnetic moxibustion device is firmly bonded on the patient's skin and is easy to use, thus, the magnetic moxibustion device can be simultaneously fixed on different sites of the patient's body and can carry out simultaneously moxibustion, without subjecting to the point layout of the human body.

(5) The moxibustion canister of the magnetic moxibustion device can adjust the air flow by providing the air inlets and the air outlets, and can ensure that other parts of the moxibustion canister have better seal, so that the moxa column of the same specification and a better moxibustion therapy effect.

(6) The magnetic moxibustion device is of a simple structure and is easy to install. The moxibustion canister itself and its internal components have flame retardant function and are safety to use, so, after doctors teach the patient himself can carry out moxibustion at home when the patient may not go out inconveniently or may carry out health care cure.

By using the traditional moxa to carry out moxibustion, a magnetic moxibustion device according to the present invention essentially remains consistent with the traditional moxibustion. When the magnetic moxibustion device is used for moxibustion, the combustion speed of the moxa column can be adjusted by adjusting the size of the air outlets, so that the moxibustion temperature and the moxibustion time can be adjusted. In addition, the magnetic moxibustion device is convenient to use, is well-ventilated, can adequately burn the moxa column, and can produce less smog, and security isolation is kept between the moxa column and the skin during moxibustion, without causing the patient to scald, bubble, infect and so on.

Figure 1:
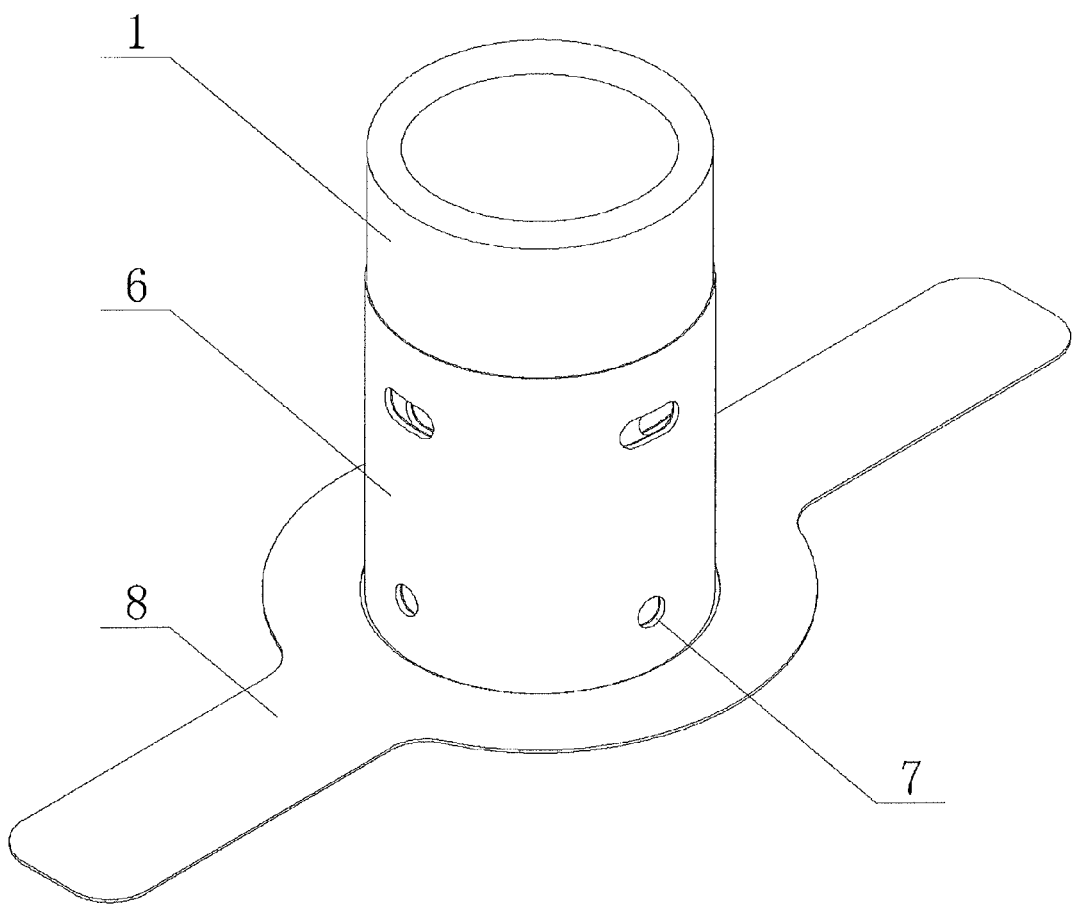
FIG. 1 is a schematic view of a first embodiment according the present invention in use.
Figure 2:
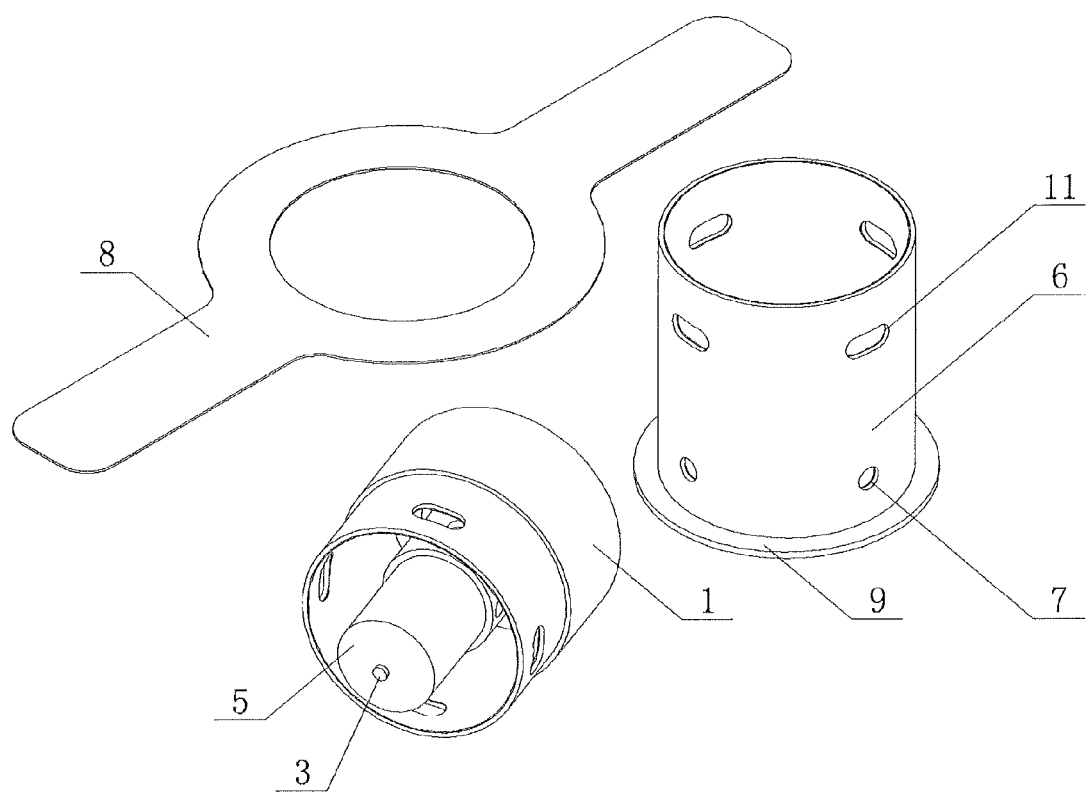
FIG. 2 is a schematic view of the first embodiment in assembly.
Figure 3:
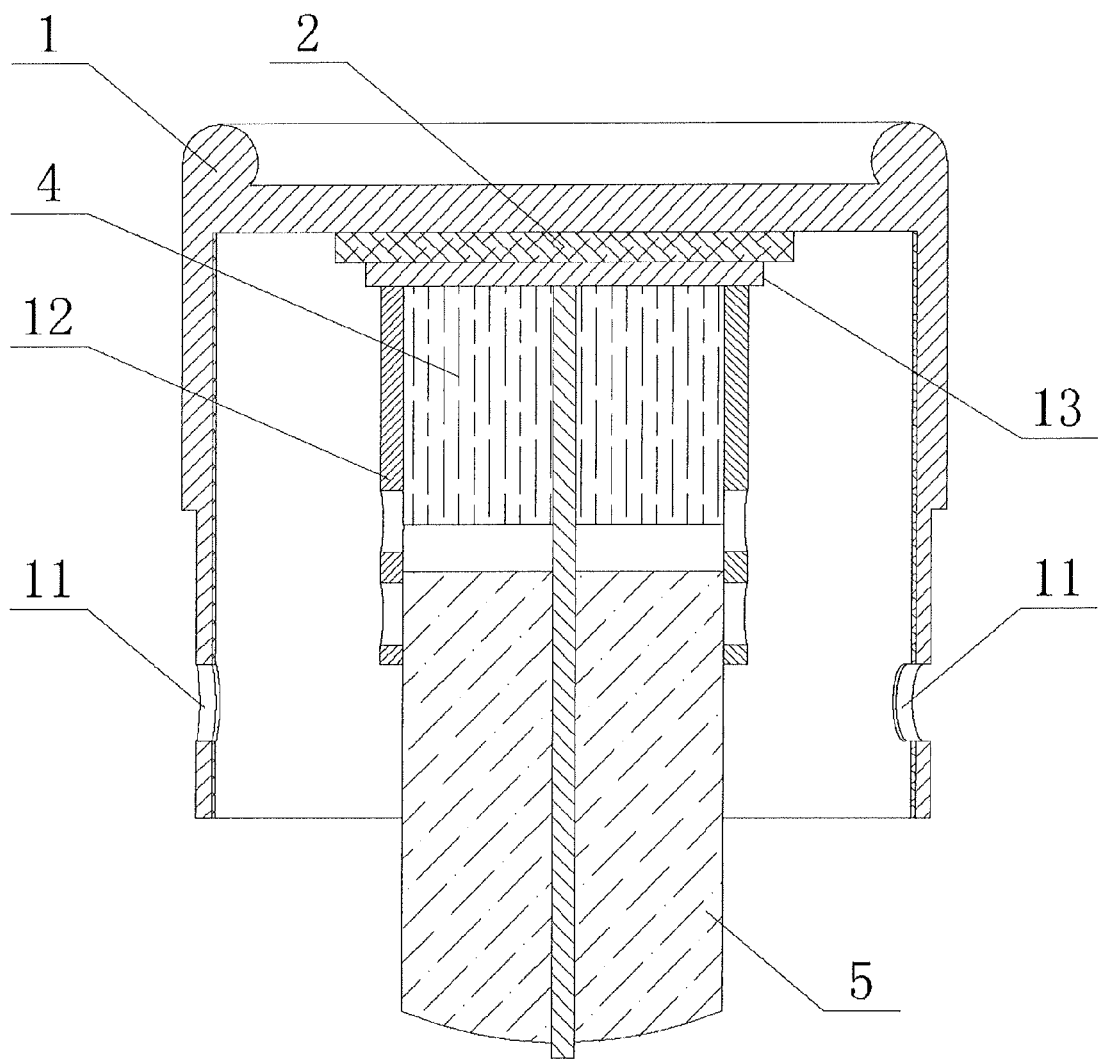
FIG. 3 is a sectional view of a moxibustion canister lid as indicated by the number 1 in FIG. 2.
Figure 4:
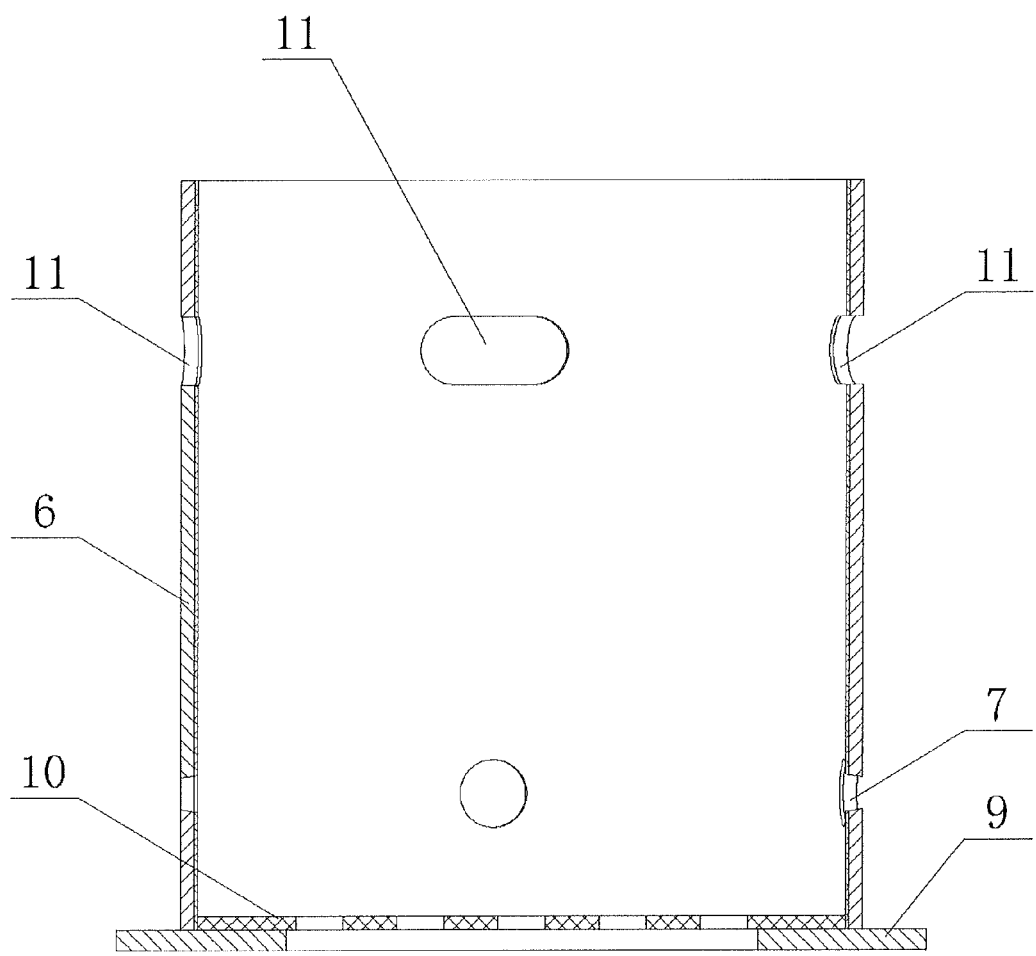
FIG. 4 is a sectional view of a moxibustion canister body as indicated by the number 6 in FIG. 2.
Figure 5:
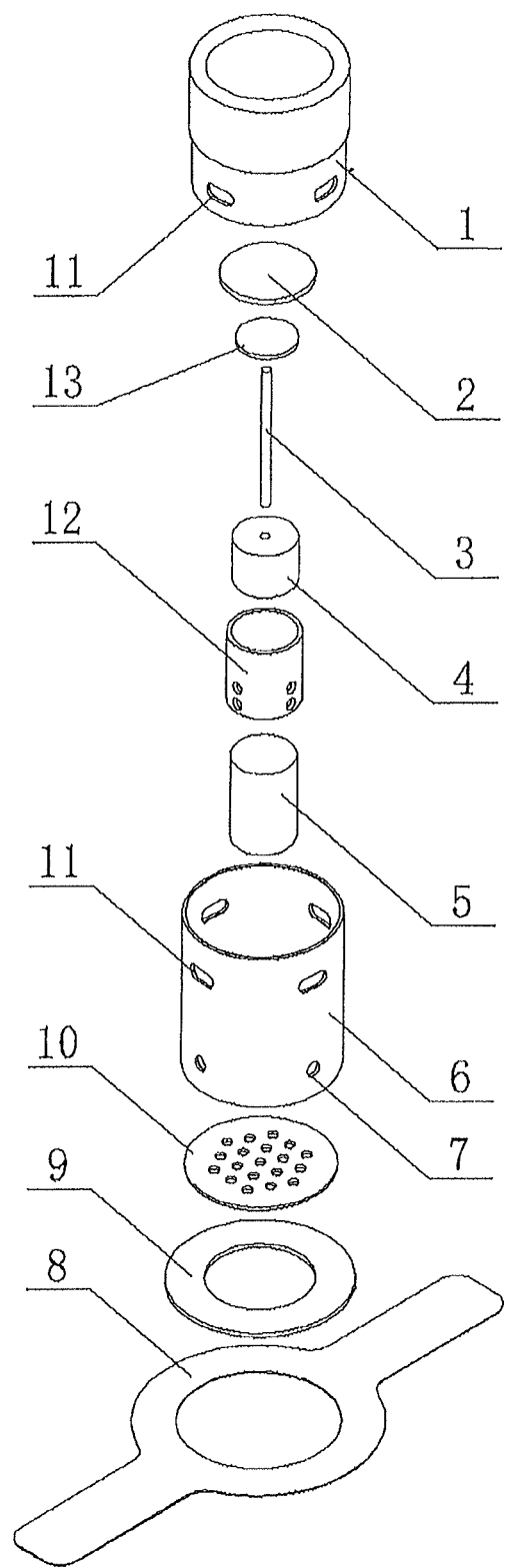
FIG. 5 is a schematic exploded view of the first embodiment.

In the figures: 1, moxibustion canister lid, 2. fixing sheet, 3. magnet guiding needle, 4. wood block, 5. moxa column, 6. moxibustion canister body, 7. air inlet, 8. medical adhesive tape, 9. moxibustion seat, 10. partition, 11. air outlet, 12. moxa column fixing sleeve, 13, movable sheet, 14. clamp spring, 15. snap ring.

SPECIFIC MODE FOR CARRYING OUT THE INVENTION

In order to further set forth the technical means which the present invention takes for the intended purpose and efficiency achieved, the structures, features and efficiencies of the present invention are described in detail below taken in conjunction with the attached figures and the preferred embodiments.

Example 1

Example 1 of the present invention is shown in FIGS. 2, 3, 4 and 5. In this example, the magnetic moxibustion device includes a moxibustion canister body 6 and a moxibustion canister lid 1 which hermetically covers the upper end of the moxibustion canister body 6.

A moxa column mounting base for hanging moxa column 5 is detachably installed on the internal surface of the top wall of moxibustion canister lid 1 by a magnetic attraction structure, wherein, the magnetic attraction structure is comprised of a movable portion and a fixed portion, particularly a pair of magnetic sheets or one magnetic sheet and one ferromagnetic metal sheet, one of which acts as a fixed sheet 2 fixed on the top wall of the moxibustion canister lid 1, and the other acts as a movable sheet 13 fixed together with the moxa column mounting base. The fixed sheet 2 may be bonded on the top wall of the moxibustion canister lid 6 by a high-temperature resistant environmentally safe adhesive.

A magnet guiding needle 3 is fixed on the movable sheet 13 and extends perpendicularly to the surface of the movable sheet 13 toward the lower end of the moxibustion canister body 6. The magnet guiding needle 3 passed through the moxa column 5. The magnetic field of the magnetic attraction structure is guided out of the lower end of the moxibustion canister through the magnet guiding needle 3, and is applied to the human body moxibustion application position, so as to perform the moxibustion therapy and the magnet therapy at the same time.

The moxa column mounting base provided on the internal surface of the top wall of the moxibustion canister 1 consists of the movable sheet 13, the magnet guiding needle 3, and a moxa column fixing sleeve 12. The moxa column fixing sleeve 12 at one end is fixed together with the movable sheet 13. The magnet guiding needle 3 is located within the moxa column fixing sleeve 12. The moxa column fixing sleeve 12 has an internal diameter slightly less than the external diameter of the moxa column 5, so that the moxa column 5 is inserted in and fixed to the moxa column fixing sleeve 12 via one end, and at the same time, the magnet guiding needle 3 is inserted in the moxa column 5.

The magnet guiding needle 3 axially extends through the moxa column 5 from the top down. Ash produced by the combustion of the moxa column 5 is collected around the magnet guiding needle 3 on the basis of the side of the magnet guiding needle 3 encircled by the moxa column 5, thereby avoiding its falling and scalding the patient.

In the moxa column fixing sleeve 12 is provided with a moxa column heat-insulated structure for obstructing heat during the combustion of the moxa column 5 from transferring to the top wall of the moxibustion canister lid 1; the heat-insulated structure is made of cylindrical wood block 4.

On a side wall of the moxa column fixing sleeve 12 is further provided with a through hole for discharging high-temperature gas produced within the moxa column fixing sleeve 12 during the combustion of the moxa column 5. A gap is formed between the endface of one end where the moxa column 5 is inserted into the moxa column fixing sleeve 12 and the lower endface of the moxa column heat-insulated structure. The gap communicates with the through hole, both of them facilitating the combustion of the moxa column 5.

A side wall of the moxibustion canister 6 is provided with several air inlets 7 in peripheral and uniform distribution close to the lower end of the moxibustion canister, and is provided with several air outlets 11 in peripheral and uniform distribution close to the upper end thereof; during the combustion of the moxa column 5, air enters from the gas inlets 7 and exits from the gas outlets 11.

Both the moxibustion canister body 6 and the moxibustion canister lid 1 are of a cylindrical shape. The gas inlets 7 and the gas outlets 11 include a number of, preferably 2-6, inlets and outlets peripherally uniformly distributed on the moxibustion canister body 6, respectively.

The moxibustion canister lid 1 is inserted in the upper end of the moxibustion canister body 6 via a section of canister wall of itself thereof. The gas outlets 11 are positioned at the location where the moxibustion canister body 6 overlaps with the moxibustion canister lid 1, and radially extend through both the moxibustion canister body 6 and the moxibustion canister lid 1, so that the moxibustion canister lid 1 can be rotated relative to the moxibustion canister body 6, thereby adjusting the opening size of the gas outlets 11 and controlling air flow within the moxibustion canister body 6, and therefore controlling the combustion speed of the moxa column 5 for the purpose of adjusting the moxibustion temperature.

At the lower end of the moxibustion canister body 6 is provided a ring-shaped moxibustion seat 9 with an opening in the middle. On the lateral surface of the moxibustion seat 9 facing the moxibustion canister body 6 is provided a screen partition 10 for covering the opening in the middle, in which a number of through holes are thickly distributed. The moxibustion therapy generated during the combustion of the moxa column 5 can act on the moxibustion site of the human body through the through holes in the screen partition. The screen partition 10 is positioned on the upper surface of the moxibustion seat 9, which can effectively separate the lower surface of the partition 10 from the human skin so as to avoid burn or scald. In addition, the through holes in the screen partition 10 may not have an excessive hole size so that ash produced by the combustion of the moxa column 5 is prevented from falling onto the human skin by the through holes, which may cause burn or scald.

On each of the inner surfaces of the moxibustion canister body 6, the moxibustion canister lid 1, the moxibustion seat 9, and the screen partition 10, is provided with a heat reflecting film having flame retardant characteristic. In this way, not only the loss of heat of the magnetic moxibustion device is reduced and the moxibustion therapy effect is improved, but also the usage safety of the magnetic moxibustion device is enhanced.

In order to facilitate the usage of the magnetic moxibustion device, a medical adhesive tape 8 is arranged on the magnetic moxibustion device, and is sleeved on the moxibustion canister body 6 via a through hole thereon. The ring-shaped moxibustion seat 9 has a flange matching with the medical adhesive tape 8 and radially projecting from the external surface of the moxibustion canister body 6. The medical adhesive tape 8 fixes the whole magnetic moxibustion device to the moxibustion site of the patient by pressing against the upper surface of the flange.

Instead of providing the moxa column fixing sleeve 12, the above moxa column mounting base may only consists of the movable sheet 13 and the magnet guiding needle 3. In this case, the moxa column 5 is inserted in the magnet guiding needle 3, and its position then is determined by changing the insertion depth of the magnet guiding needle 3.

Each of the moxibustion canister body 6, the moxibustion canister lid 1, and the moxa column fixing sleeve 12 is made of relative hard paperboard.

In using the above magnetic moxibustion device, first, the moxa column 5 is fixed on the moxa column fixing sleeve 12, and after firing the moxa column 5, the moxibustion canister lid 1 hermetically covers the moxibustion canister body 6, then, the magnetic moxibustion device is fixed on the moxibustion site of the human body by means of the medical adhesive tape 8, and the moxibustion canister body 6 is rotated relative to the moxibustion canister lid 1 so that the moxa column 5 is adjusted to a proper combustion speed and the moxibustion is carried out.

Figure 6:
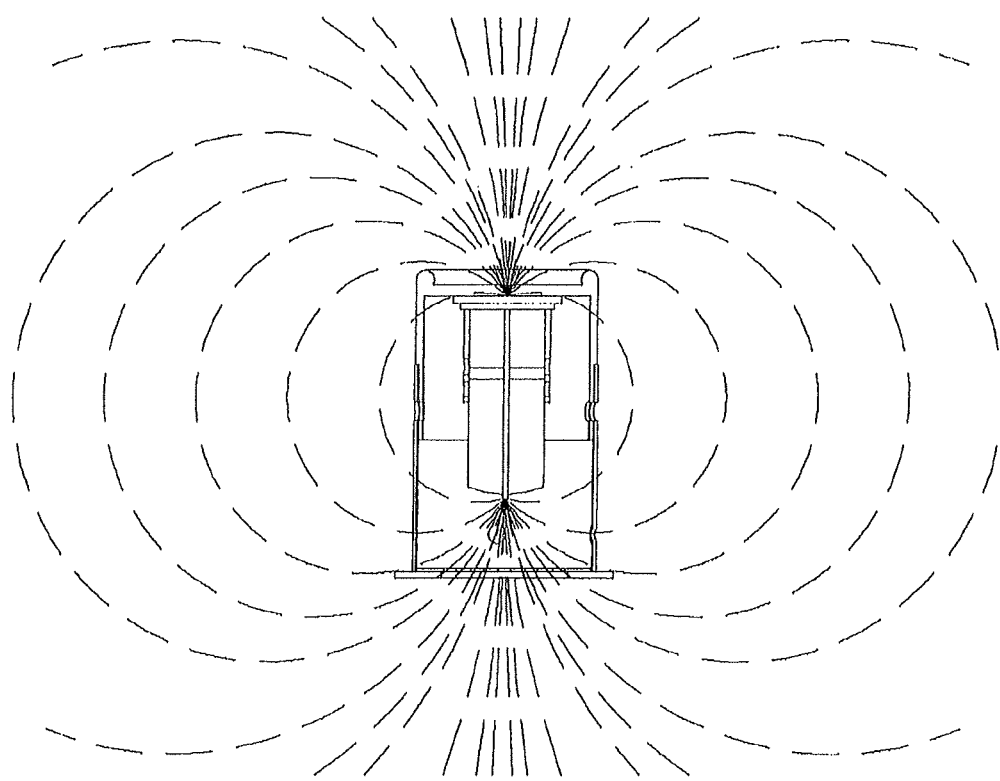
FIG. 6 is a schematic view of the distribution of the magnetic field in the first embodiment.

As shown in FIG. 6, during the moxibustion, the magnetic moxibustion device according to the present invention, in addition to the moxibustion therapy action produced during combustion of the moxa column 5, carries out magnetic therapy on the moxibustion site of the human body via the magnetic field, thereby producing the combination effect of the moxibustion therapy and the magnetism therapy.

Example 2

Figure 7:
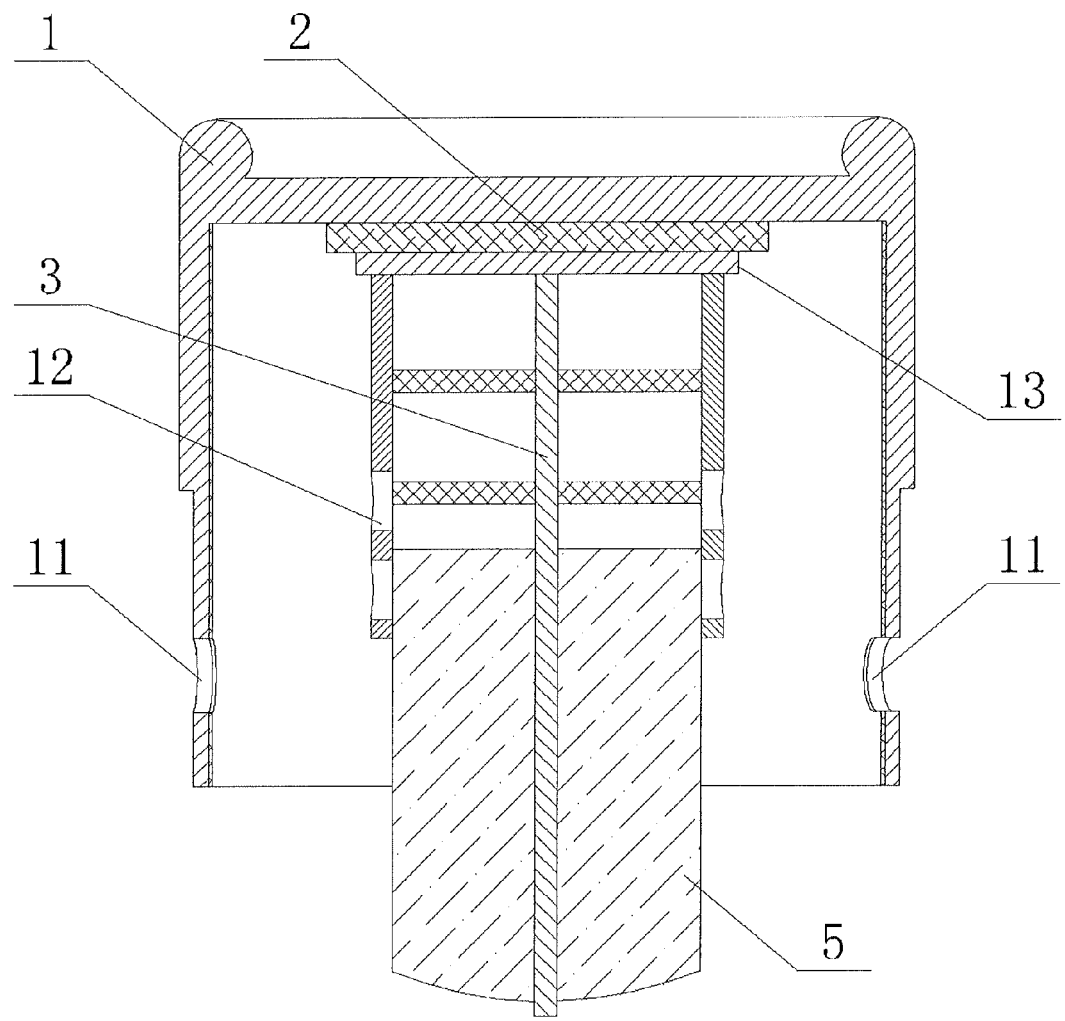
FIG. 7 is a partial structural schematic view of the second embodiment according to the present invention.

Example 2 is shown in FIG. 7, which differs from example 1 in that the moxa column heat-insulated structure in the moxa column fixing sleeve 12 is formed by a thermal baffle. In order to ensure heat insulation effect of the thermal baffle, one to three layers of thermal baffles may be provided in the moxa column fixing sleeve 12, so that one to three layers of heat-insulated spaces are divided above the upper endface of the moxa column 5, which cooperates with the thermal baffles so as to better isolate the combustion temperature of the moxa column 5.

Example 3

Figure 8:
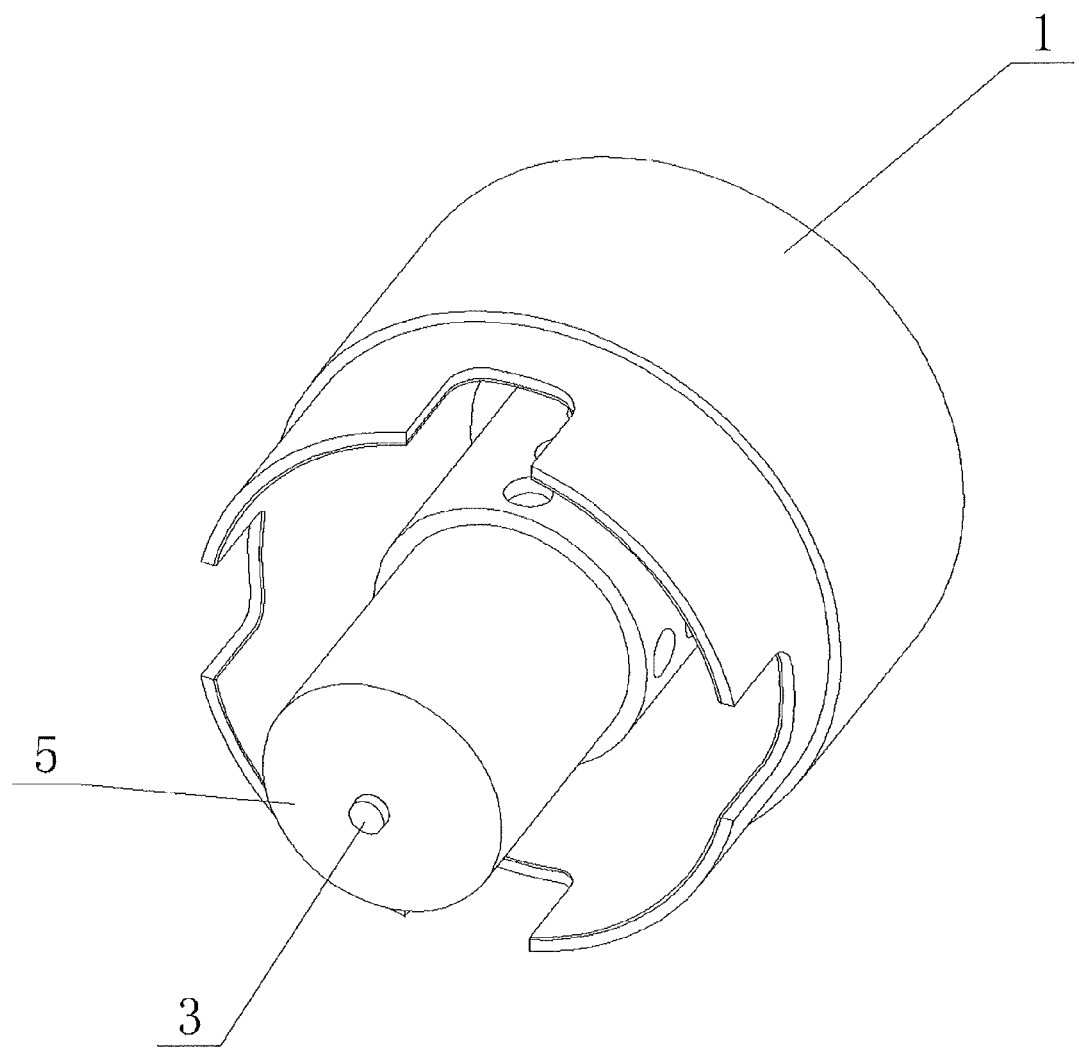
FIG. 8 is a partial structural schematic view of the third embodiment according to the present invention.

Example 3 is shown in FIG. 8, which differs from example 1 in that in this example, the portion of air outlets 11 extending through the moxibustion canister lid 1 is shaped as groove. With this groove, it is also achieved that the opening size of the air outlets 11 can be adjusted.

Example 4

Figure 9:
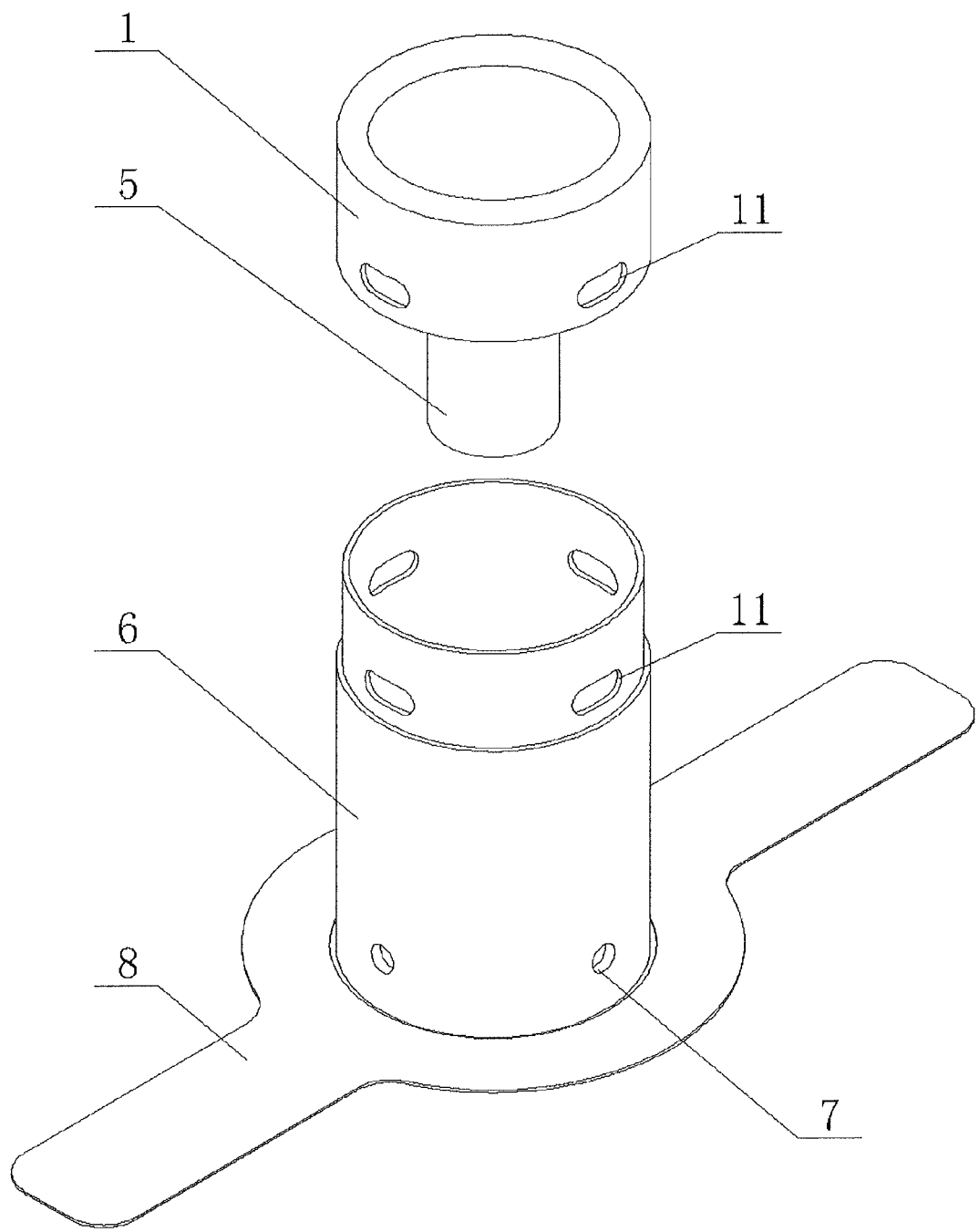
FIG. 9 is a structural schematic view of the forth embodiment according to the present invention.

Example 4 is shown in FIG. 9, which differs from example 1 in that in this example, the moxibustion canister lid 1 hermetically covers the upper end of the moxibustion canister body 6 in a sleeving way. The air outlets 11 are positioned at the location where the moxibustion canister body 6 overlaps with the moxibustion canister lid 1. Similarly, by rotating the moxibustion canister lid 1 relative to the moxibustion canister body 6, the opening size of the air outlets 11 can be adjusted.

Example 5

Figure 10:
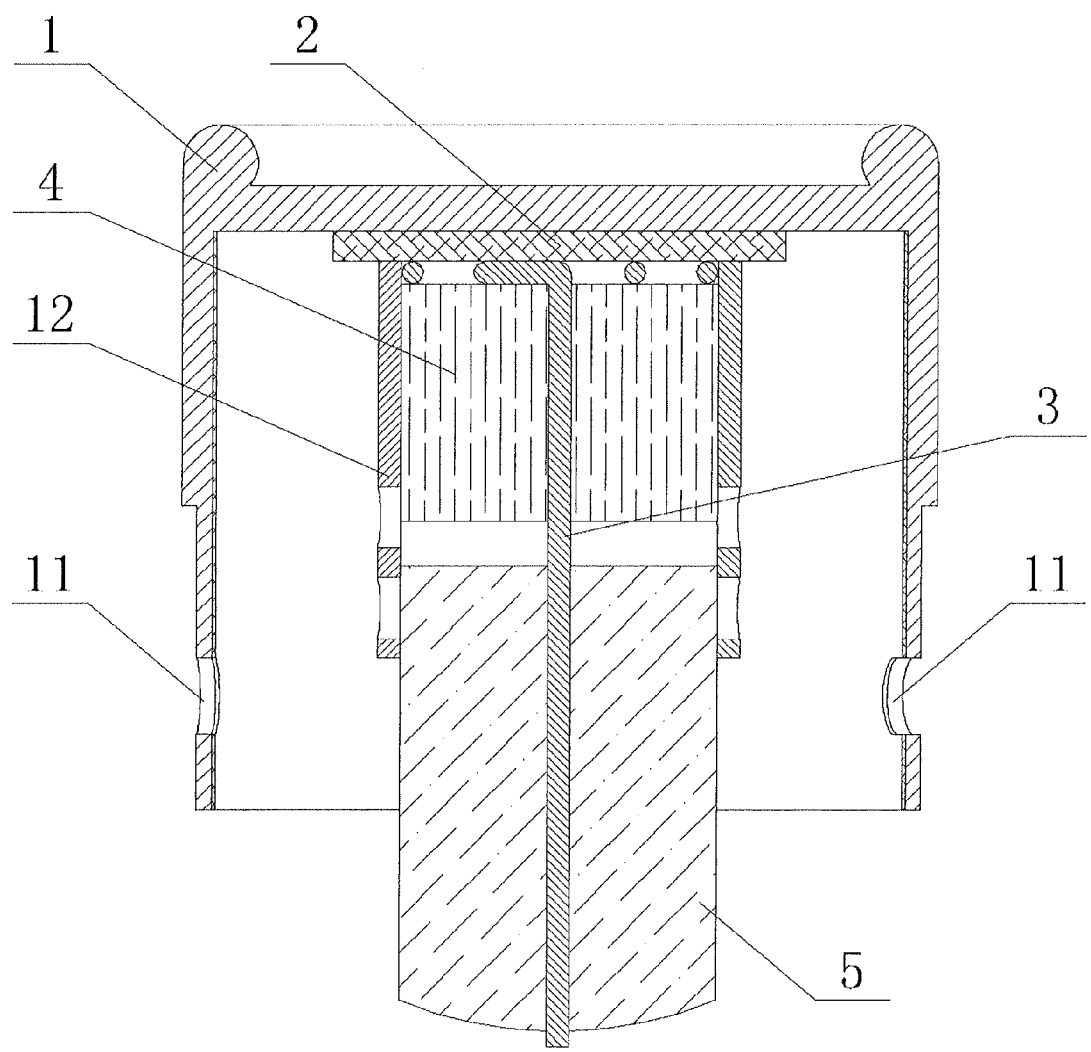
FIG. 10 is a structural schematic view of the fifth embodiment according to the present invention.

Example 5 is shown in FIG. 10, which differs from example 1 in that in this example, both the movable portion of the magnetic attraction structure and the magnet guiding needle 3 are made of ferromagnetic material, and the movable portion is directly formed of a metal ring manufactured by bending the upper end of the magnet guiding needle 3. The metal ring positioned on the upper end of the magnet guiding needle 3 can facilitate the installation thereof on the fixed portion.

Example 6

Figure 11:
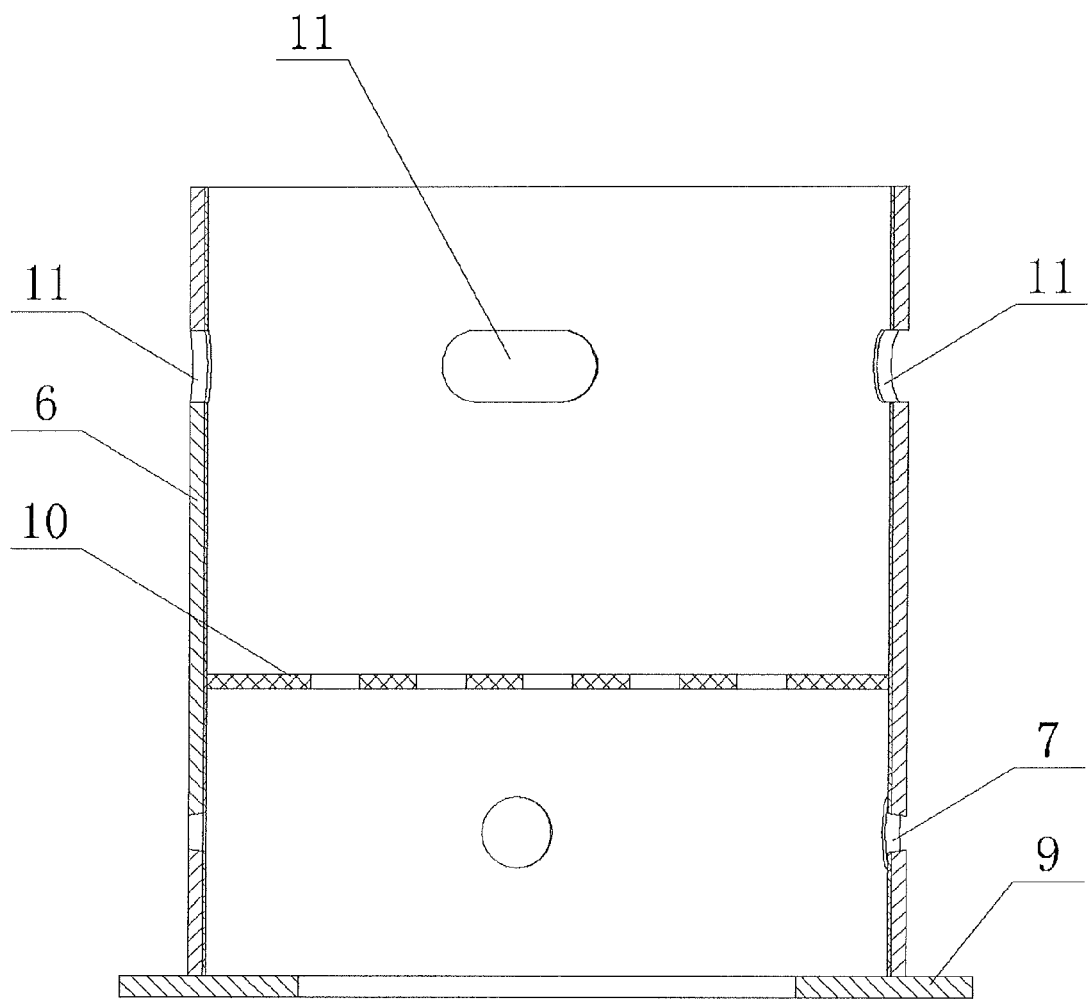
FIG. 11 is a structural schematic view of the sixth embodiment according to the present invention.

Example 6 is shown in FIG. 11, which differs from example 1 in that in this example, the screen partition 10 has a gap from the lower end of the moxibustion canister body 6 to ensure that it can not be in contact with the skin at the moxibustion site of the human body. Thus, the safety of the magnetic moxibustion device is enhanced by raising the screen partition 10 in height.

Example 7

Figure 12:
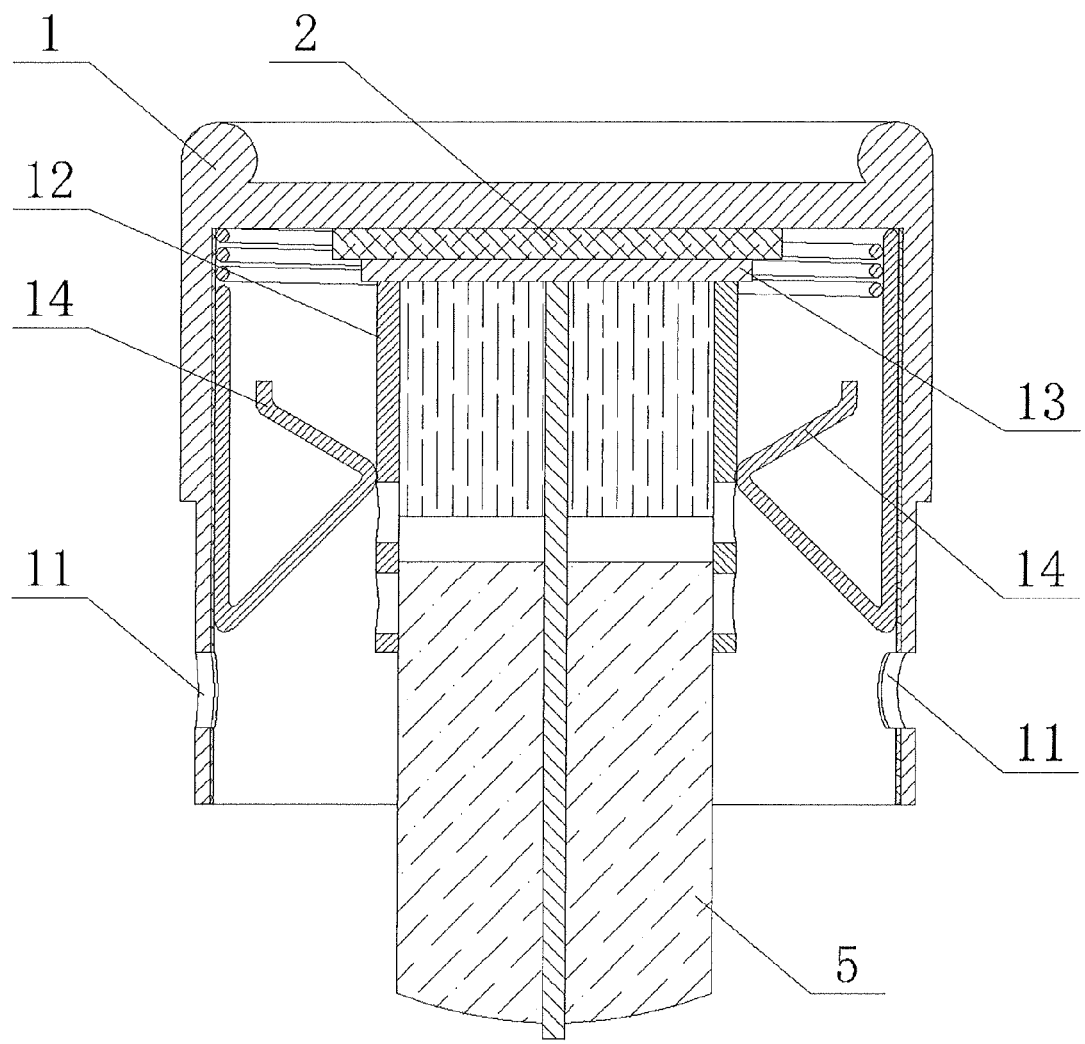
FIG. 12 is a structural schematic view of the seventh embodiment according to the present invention.

Example 7 is shown in FIG. 12, which differs from example 1 in that in this example, a clamp spring 14 is provided within the moxibustion canister lid 1. A seat ring on the upper portion of the clamp spring 14 is bonded on the top wall of the moxibustion canister lid 1 and an elastic claw on the lower portion clamps the moxa column fixing sleeve 12, thereby preventing the moxa column mounting base from waggling or accidently disengaging due to the unsteady attraction between the movable portion and the fixed portion.

Example 8

Figure 13:
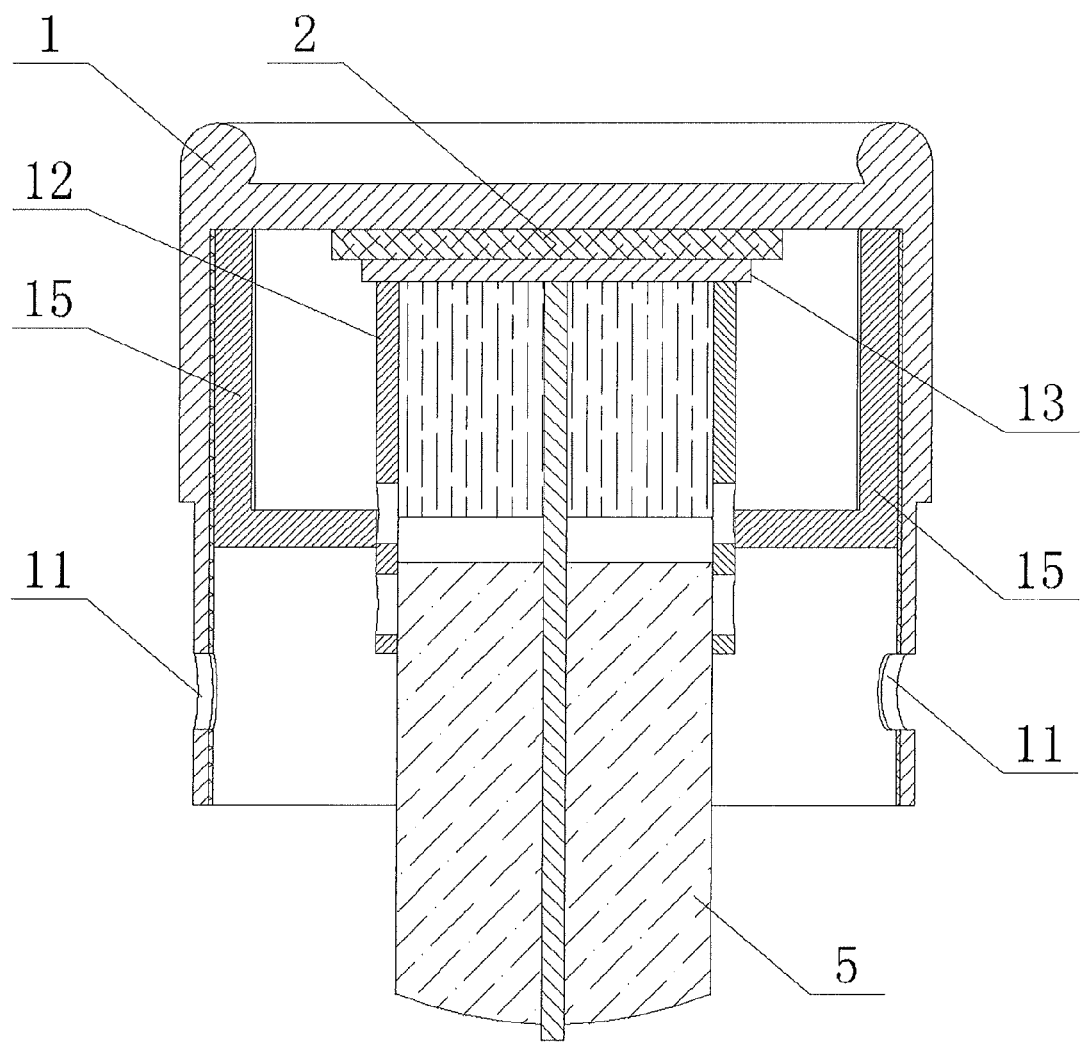
FIG. 13 is a structural schematic view of the eighth embodiment according to the present invention.
Figure 14:
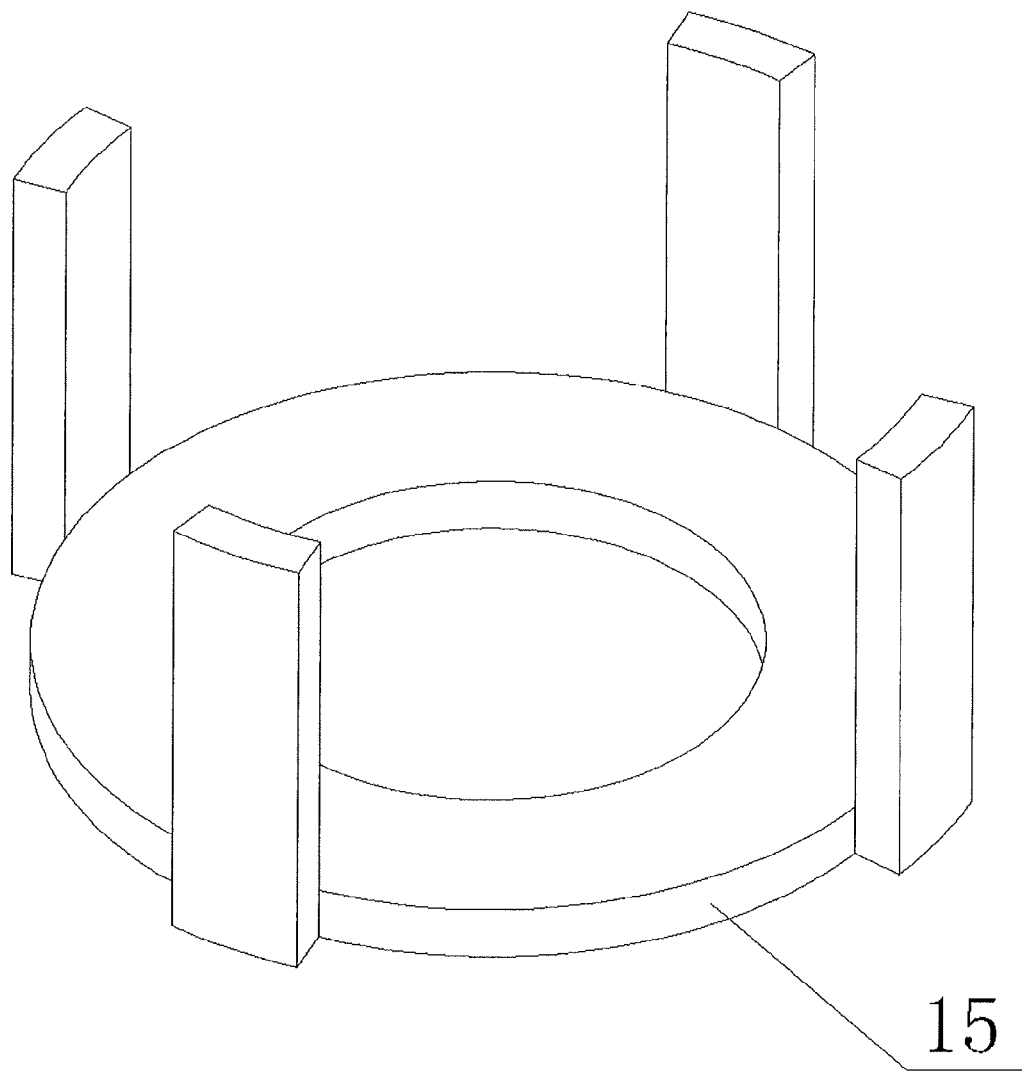
FIG. 14 is a structural schematic view of a snap ring used by the eighth embodiment according to the present invention.

Example 8 is shown in FIGS. 13 and 14, which differs from example 1 in that in this example, a snap ring 15 is provided within the moxibustion canister lid 1. The snap ring 15 in the middle is provided with a center bore matching with the moxa column fixing sleeve 12. A leg on a side of the snap ring 15 is bonded to the side wall or top wall of the moxibustion canister lid 1. The center bore in the middle of the snap ring 15 clamps the moxa column fixing sleeve 12, thereby preventing the moxa column mounting base from waggling or accidently disengaging due to the unsteady attraction between the movable portion and the fixed portion.

Example 9

Figure 15:
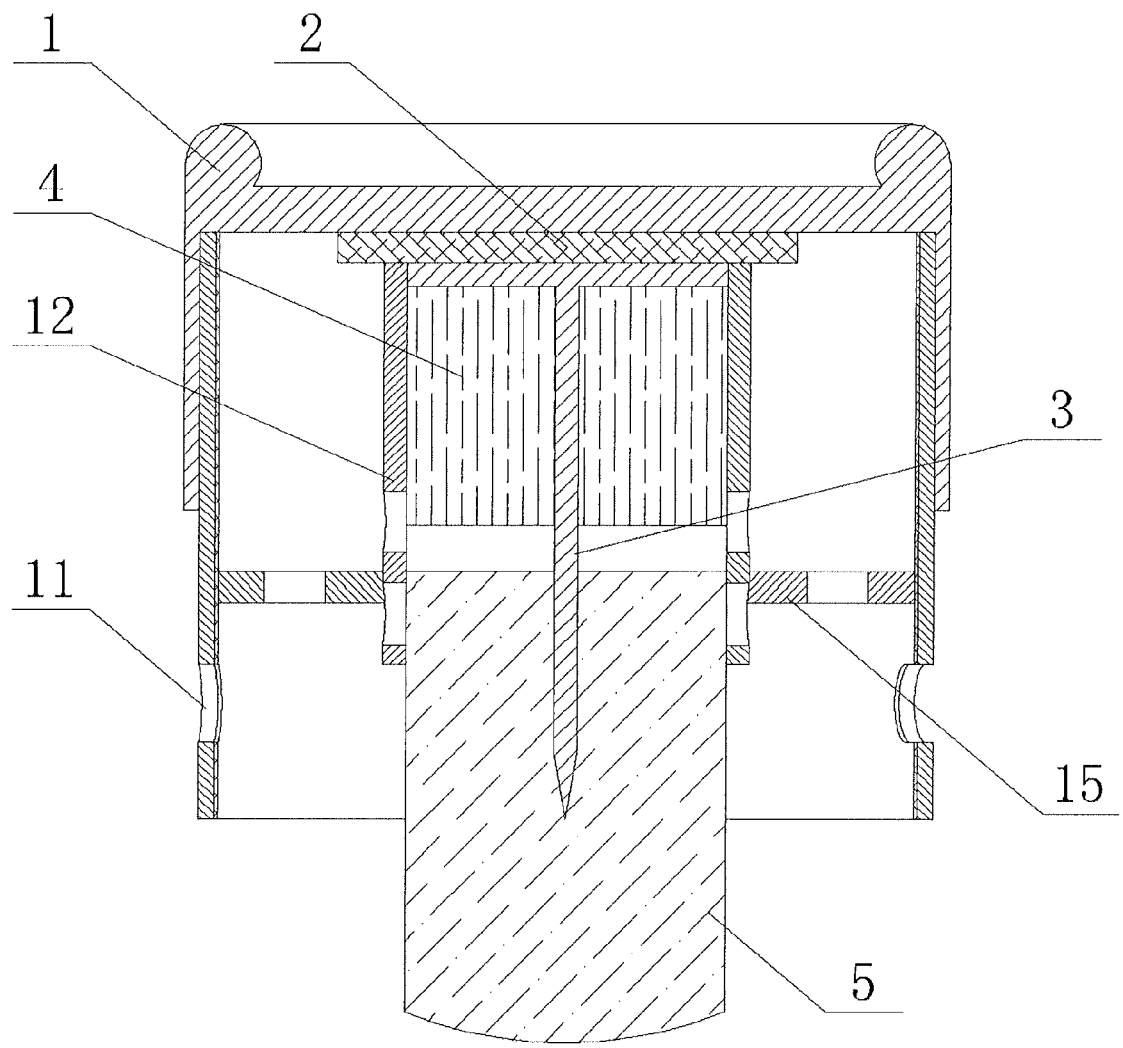
FIG. 15 is a structural schematic view of the ninth embodiment according to the present invention.

Example 9 is shown in FIG. 15, which differs from example 8 in that in this example, the moxa column mounting base is comprised of a fixed sheet 2 made of a magnetic sheet and a moxa column fixing sleeve 12. The upper end of the moxa column mounting base is adhesively fixed to the top wall of the moxibustion canister via the fixed sheet 1.

The upper end of the moxa column fixing sleeve 12 is adhesively fixed to the fixed sheet 2, so as to firmly install the moxa column 5.

A magnet guiding needle 3 is provided within the moxa column mounting base. The magnet guiding needle 3 passes through the moxa column 5 with its depth of at least one third of the full-length of the moxa column; the top end of the magnet guiding needle 3 has a ferromagnetic sheet for attracting the magnet guiding needle 3 onto the fixed sheet 2. The ferromagnetic sheet and the magnet guiding needle 3 are formed integrally and may in whole be made of ferromagnetic material, thereby having better magnetic conductivity.

A snap ring 15 is provided within the moxibustion canister lid 1. The snap ring 15 in the middle is provided with a center bore matching with the moxa column fixing sleeve 12, around which are uniformly distributed breathing holes, a side of the snap ring 15 is bonded to a side wall of the moxibustion canister lid 1. The center bore in the middle of the snap ring 15 clamps the moxa column fixing sleeve 12, thereby preventing the moxa column mounting base from waggling or accidently disengaging in replacing the moxa column 5.

The above description is only intended to illustrate the present invention. It is appreciated that the present invention is not limited to the above embodiments. Various modifications according to the inventive concept fall within the protection scope of the present invention.

The invention claimed is:

1. A magnetic moxibustion device comprising:
a moxibustion canister with a sealed upper end,
wherein a moxa column is hung in the moxibustion canister through a moxa column mounting base,
an upper end of the moxa column mounting base is mounted on a top wall of the moxibustion canister in a detachable manner through a magnetic attraction structure,
a magnet guiding needle extending toward a lower end of the moxibustion canister is disposed in the moxa column mounting base and the magnet guiding needle passes through the moxa column wherein a magnetic field of the magnetic attraction structure is guided out of the lower end of the moxibustion canister through the magnet guiding needle, and is capable of being applied to a human body moxibustion application position, so as to perform a moxibustion therapy and a magnet therapy at a same time.

2. The magnetic moxibustion device according to claim 1, wherein said magnetic attraction structure comprises a movable portion and a fixed portion, at least one of which is made of magnet material, wherein the movable portion and the fixed portion are detachably connected to with each other in a mutual attraction way, the fixed portion is fixed onto the top wall of the moxibustion canister, the movable portion is fixed to the upper end of the moxa column mounting base, and the magnet guiding needle is connected to the movable portion.

3. The magnetic moxibustion device according to claim 2, wherein both of the movable portion of the magnetic attraction structure and the magnet guiding needle are made of ferromagnetic material and the movable portion is directly formed of a metal ring manufactured by bending an upper end of the magnet guiding needle.

4. The magnetic moxibustion device according to claim 3, wherein the moxa column mounting base is only formed by the magnet guiding needle without a moxa column fixing sleeve, and the moxa column is hung in the moxibustion canister by inserting the magnet guiding needle into the moxa column.

5. The magnetic moxibustion device according to claim 2, wherein both the fixed portion and the movable portion of the magnetic attraction structure are in a form of a sheet structure, thereby forming corresponding fixed sheet and movable sheet respectively.

6. The magnetic moxibustion device according to claim 5, wherein the moxa column mounting base is only formed by the magnet guiding needle without a moxa column fixing sleeve, and the moxa column is hung in the moxibustion canister by inserting the magnet guiding needle into the moxa column.

7. The magnetic moxibustion device according to claim 5, wherein the moxa column mounting base includes a moxa column fixing sleeve, the movable sheet is fixed with an upper end of the moxa column fixing sleeve, the magnet guiding needle is located within the moxa column fixing sleeve, and the moxa column is inserted in the moxa column fixing sleeve through one end thereof.

8. The magnetic moxibustion device according to claim 7, wherein the moxa column fixing sleeve is provided with a heat-insulated structure for obstructing heat when the combustion of the moxa column is transferred to the movable sheet, wherein the heat-insulated structure is formed by a partition or cylindrical block provided within the moxa column fixing sleeve.

9. The magnetic moxibustion device according to claim 8, wherein a side wall of the moxa column fixing sleeve is provided with a through hole for discharging high-temperature gas produced within the moxa column fixing sleeve during combustion of the moxa column.

10. The magnetic moxibustion device according to claim 7, wherein the moxibustion canister is provided with a clamp spring or a snap ring with a center bore, the clamp spring or the snap ring is adhesively fixed to the top wall or a side wall of the moxibustion canister and clips the moxa column fixing sleeve, and the moxa column fixing sleeve is radially and detachably fixed by the clamp spring or the snap ring.

11. The magnetic moxibustion device according to claim 10, wherein the magnet guiding needle is inserted to at least one third of the full-length of the moxa column or is inserted through the moxa column from a top face of the moxa column toward a bottom face of the moxa column.

12. The magnetic moxibustion device according to claim 3, wherein the magnet guiding needle is inserted to at least one third of the full-length of the moxa column or is inserted through the moxa column from a top face of the moxa column toward a bottom face of the moxa column.

13. The magnetic moxibustion device according to claim 1, wherein the moxibustion canister is a cylindrical barrel, a side wall of the moxibustion canister is provided with a plurality of air inlets in a peripheral and uniform distribution, and is provided with a plurality of air outlets in a peripheral and uniform distribution.

14. The magnetic moxibustion device according to claim 13, wherein the moxibustion canister consists of a moxibustion canister body and a moxibustion canister lid, the moxibustion canister lid hermetically covers an upper end of the moxibustion canister body in an inserting or sleeving way, and partly overlaps with the moxibustion canister along an axis of the moxibustion canister body, the plurality of air outlets are positioned at a location where the moxibustion canister body overlaps with the moxibustion canister lid, and radially extend through both the moxibustion canister body and the moxibustion canister lid, so that the moxibustion canister lid is rotatable relative to the moxibustion canister body, thereby adjusting an opening size of the plurality of air outlets.

15. The magnetic moxibustion device according to claim 14, wherein within the moxibustion canister body there is a screen partition which is positioned beneath the moxa column and a gap positioned between the screen partition and a lower end of the moxibustion canister body to ensure that the screen partition is not capable to be in contact with a skin at the human body moxibustion application position.

16. The magnetic moxibustion device according to claim 15, wherein, on inner surfaces of each of the moxibustion canister body, the moxibustion canister lid and the screen partition, a heat reflecting film having a flame retardant characteristic is provided.

17. The magnetic moxibustion device according to claim 14, wherein, at the lower end of the moxibustion canister body is provided with a ring-shaped moxibustion seat radially projecting from an exterior surface of the moxibustion canister body, and a medical adhesive tape is sleeved on the moxibustion canister body and can fix the whole magnetic moxibustion device to a human body moxibustion application position by pressing against an upper surface of the ring-shaped moxibustion seat.

18. A magnetic moxibustion device including a moxa column combustion chamber, the moxa column combustion chamber comprising:

a moxibustion canister, and a moxibustion canister lid hermetically covering the moxibustion canister, such that a moxa column can be hung in the moxibustion canister lid through a moxa column mounting base, wherein the moxa column mounting base comprises a magnetic sheet and a moxa column fixing sleeve, an upper end of the moxa column mounting base is adhesively fixed to a top wall of the moxibustion canister lid via the magnetic sheet, and wherein a magnet guiding needle extending toward a lower end of the moxibustion canister is disposed in the moxa column mounting base, wherein the magnet guiding needle passes through the moxa column, wherein, a magnetic field of the magnetic sheet is guided out of the lower end of the moxibustion canister through the magnet guiding needle, and is capable to be applied to a human body moxibustion application position, so as to perform a moxibustion therapy and a magnet therapy at a same time.

19. The magnetic moxibustion device according to claim 18, wherein an upper end of the moxa column fixing sleeve is adhesively fixed to the magnetic sheet, a heat-insulated structure is disposed inside the moxa column fixing sheet for obstructing heat during combustion of the moxa column transferring to the magnetic sheet, and the heat-insulated structure is formed by a cylindrical block provided within the moxa column fixing sleeve; the magnet guiding needle is provided within the moxa column fixing sleeve, a top end of the magnet guiding needle has a ferromagnetic sheet for attracting the magnet guiding needle onto the magnetic sheet, the ferromagnetic sheet and the magnet guiding needle are formed integrally; on a side wall of the moxa column fixing sleeve is provided with a through hole for discharging high-temperature gas produced within the moxa column fixing sleeve during the combustion of the moxa column.

20. The magnetic moxibustion device according to claim 18, wherein the moxibustion canister lid is provided with a clamp spring or a snap ring with a center bore, the clamp spring or the snap ring is adhesively fixed a top wall or a side wall of the moxibustion canister lid and clips the moxa column fixing sleeve, and the moxa column fixing sleeve is radially and detachably fixed by the clamp spring or the snap ring.

* * * * *